United States Patent [19]

Ward

[11] 4,358,456
[45] Nov. 9, 1982

[54] ANTIPSYCHOTIC PIPERIDINOMETHYL-INDOLE DERIVATIVES

[75] Inventor: Terence J. Ward, Slough, England

[73] Assignee: John Wyeth & Brother Limited, Maidenhead, England

[21] Appl. No.: 257,829

[22] Filed: Apr. 27, 1981

[30] Foreign Application Priority Data

May 3, 1980 [GB] United Kingdom ................ 8014938

[51] Int. Cl.³ .................. A61K 31/445; C07D 401/06
[52] U.S. Cl. ..................................... 424/267; 546/201
[58] Field of Search ........................ 546/201; 424/267

[56] References Cited

FOREIGN PATENT DOCUMENTS 42-2708  2/1967  Japan ................................. 546/201
1147887  4/1969  United Kingdom ................ 546/201

Primary Examiner—Richard A. Schwartz
Attorney, Agent, or Firm—Richard K. Jackson

[57] ABSTRACT

The invention relates to compounds of formula II

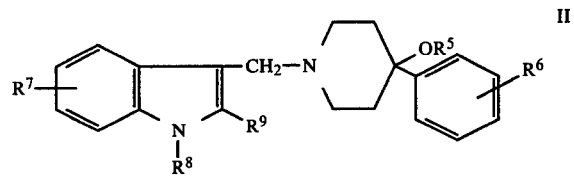

and their pharmaceutically acceptable salts wherein $R^5$ represents hydrogen, acyl, lower alkyl or cycloalkyl; $R^6$ represents hydrogen, halogen, trifluormethyl, or lower alkyl; $R^7$ represents hydrogen, lower alkyl, hydroxy, lower alkoxy, arylloweralkoxy; $R^8$ represents hydrogen or lower alkyl; and $R^9$ represents hydrogen or lower alkyl.

The compounds have dopamine blockade activity and may be used in the treatment of psychoses including schizophrenia.

7 Claims, No Drawings

ANTIPSYCHOTIC PIPERIDINOMETHYL-INDOLE DERIVATIVES

The invention relates to indole derivatives.

Japanese Patent Publication No. 2708/67 describes compounds of formula

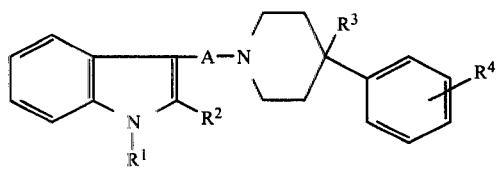

(where $R^1$ denotes hydrogen or lower alkyl, $R^2$ denotes hydrogen, a lower alkyl group or an aryl group, $R^3$ denotes a hydroxyl group, a cyano group, a carbamoyl group, an alkoxycarbonyl group, an aryl group an alkoxy group or an acylaminomethyl group, $R^4$ denotes hydrogen, halogen, a halomethyl group or a lower alkyl group and A denotes an alkylene group of 2 to 4 carbon atoms.

This Japanese application states that the above compounds of formula I have specific actions on the central nervous system and can be used as soporifics, anticonvulsants or tranquilisers or antiphlogistic agents.

During the course of our researches we have found that certain compounds, related in structure to those of formula I above, have dopamine blockade activity.

Accordingly our invention provides novel compounds of formula II

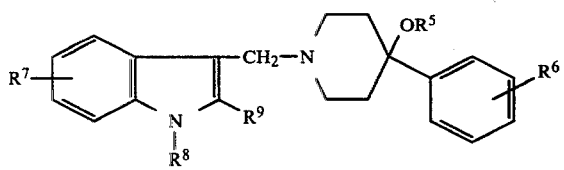

and their pharmaceutically acceptable salts wherein $R^5$ represents hydrogen, acyl, lower alkyl or cycloalkyl; $R^6$ represents hydrogen, halogen, trifluoromethyl, or lower alkyl; $R^7$ represents hydrogen, lower alkyl, hydroxy, lower alkoxy, arylloweralkoxy; $R^8$ represents hydrogen or lower alkyl; and $R^9$ represents hydrogen or lower alkyl.

The term "lower" in relation to alkyl and alkoxy radicals used herein or alkyl or alkoxy portions of a radical means that the radical or portion contains from 1 to 6 carbon atoms. Usually such radicals containing from 1 to 4 carbon atoms are preferred.

Examples of lower alkyl radicals are methyl, ethyl, n-propyl, iso-propyl, n-butyl and iso-butyl. Examples of lower alkoxy radicals are methoxy, ethoxy, propoxy and butoxy. When $R^7$ is hydroxy, lower alkoxy or arylloweralkoxy this is preferably in the 5-position.

Preferably an arylloweralkoxy radical is benzyloxy. A cycloalkyl radical preferably has from 3 to 6 carbon atoms.

Halogen may be fluorine, chlorine, bromine or iodine.

The salts of compounds of formula II may be acid addition salts formed from inorganic and organic acids e.g. sulphuric, hydrochloric, hydrobromic, hydroiodic, nitric, phosphoric, sulphonic (such as methane sulphonic and p-toluene sulphonic), acetic, maleic, fumaric, tartaric and formic acids. Quaternary ammonium salts of compounds of formula II are also included, for example those formed from lower alkyl and aryloweralkyl halides.

As a subgenus, the compounds of this invention are selected from the compounds of formula II(a)

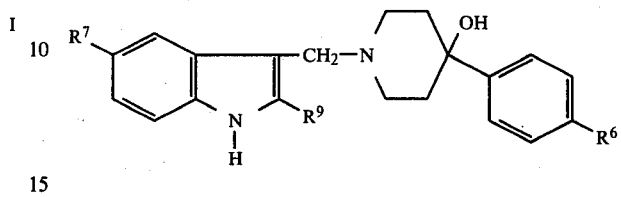

and their pharmaceutically acceptable salts wherein $R^6$ represents hydrogen, halogen, trifluoromethyl or methyl, $R^7$ represents hydrogen, methyl, hydroxy or methoxy.

The invention includes, as a novel pharmaceutical, a compound of formula II as defined above, or a pharmaceutically acceptable salt thereof. In particular the invention includes such a compound as a novel dopamine blockage agent.

When $R^5$ is acyl the acyl group is preferably loweralkylcarbonyl, cycloalkyl carbonyl or arylloweralkylcarbonyl.

The invention provides a pharmaceutical composition comprising a compound of general formula (II) or a pharmaceutically acceptable salt thereof in association with a pharmaceutically acceptable carrier. Any suitable carrier known in the art can be used to prepare the pharmaceutical composition. In such a composition, the carrier is generally a solid or liquid, or a mixture of a solid and a liquid. In some aerosol compositions the carrier may be gas.

Solid form compositions include powders, granules, tablets, capsules (e.g. hard and soft gelatin capsules), suppositaries and pessaries. A solid carrier can be, for example, one or more substances which may also act as flavouring agents, lubricants, solubilisers, suspending agents, fillers, glidants, compression aids, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) as surrounded by the carrier, which is thus in association with it. Similarly cachets are included.

Liquid form compositions include, for example, solutions, suspensions, emulsions, syrups, alixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers, preservatives, sweetners, flavouring agents, suspending agents, thickening agents, colours, viscosity regulators, stabilisers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parental administration the carrier can also be an oily ester such as ethyl oleate and isopropyl myristate. Sterile liquid carriers are used in sterile liquid form compositions for parental administration. The liquid carrier for pressurised compositions can be a halogenated hydrocarbon or other pharmaceutically acceptable propellent.

Liquid pharmaceutical compositions which are sterile solutions or suspensions can be utilised by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form. The quantity of the active ingredient in a unit dose of composition may be varied or adjusted from 0.5 mg. or less to 750 mg. or more, according to the particular need and the activity of the active ingredient. The invention also includes the compounds in the absence of the carrier where the compounds are in unit dosage form.

The invention also includes methods of preparing the compounds of formula II

The preferred method comprises reacting an indole of formula III,

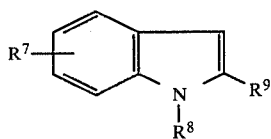

III wherein $R^7$, $R^8$ and $R^9$ are as defined above with formaldehyde and a piperidine derivative of formula IV.

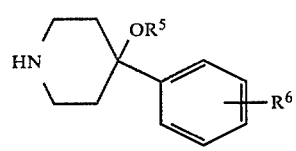

IV wherein $R^5$ and $R^6$ are as defined above and if desired converting the product to a pharmaceutically acceptable salt.

The formaldehyde used in the above reactions may be in the form of a solution in an inert solvent or as paraformaldehyde.

Alternative methods of preparing compounds of formula II are as follows:

(i) reacting a compound of formula (V)

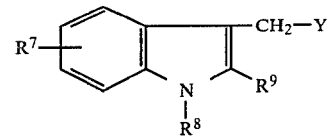

wherein Y is a halogen atom, or an equivalent replaceable atom or radical e.g. an organic sulphonyl radical such as a tosyl radical or a disubstituted amino radical such as dimethylamino or a trisubstituted ammonium radical such as trimethyl ammonium ($+NMe_3$), with a compound of formula IV as defined above;

(ii) reacting a compound of formula VI

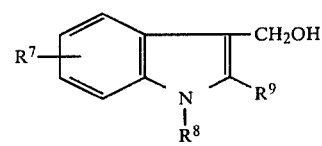

with a compound of formula IV as defined above in the presence of a catalyst e.g. Raney nickel (iii) alkylating or acylating a compound of formula II, wherein $R^5$ is hydrogen to obtain a compound of formula II, wherein $R^5$ is lower alkyl, cycloalkyl or acyl.

The product of any of the methods (i) to (iii) above may be converted to a pharmaceutically acceptable salt of the compound of formula II and isolated in this form if desired.

The invention is illustrated by the following examples.

EXAMPLE 1

1-(Indol-3-ylmethyl)-4-hydroxy-4-(p-chlorophenyl)-piperidine

Indole (0.55 g, 4.7 mmol) and 4-hydroxy-4-(p-chlorophenyl)piperidine (1.0 g, 4.7 mmol) were dissolved in glacial acetic acid (5 ml). Formaldehyde (0.36 ml, 4.8 mmol) was added with stirring and the mixture allowed to stand at room temperature for 5 hours, then poured into water and filtered. The filtrate was basified by addition of conc. ammonia to precipitate the title compound as a white solid. This turned to a yellow foam in the drying oven. (0.75 g, 47%).

The title compound was dissolved in hot iso propyl alcohol and ethereal HCl added. Solid deposited while the solution was still basic. The mixture was therefore made strongly acidic by addition of further ethereal HCl and stirred at room temperature for 2 hours. The hydrochloride of the title compound was collected and dried, m.p. 213°–214° C. Found C,62.43, H,5.62; N,7.14; $C_{20}H_{21}N_2OCl$, HCl. ½ $H_2O$ requires: C,62.18; H,6.0, N,7.25%

EXAMPLE 2

1-(Indol-3-ylmethyl)-4-hydroxy-4-phenylpiperidine

Indole (2.43 g, 0.02 mol) and 4-hydroxy-4-phenylpiperidine (3.55 g, 0.02 mol) were suspended in glacial acetic acid (20 ml) and the mixture heated gently until homogeneous. The solution was cooled in ice and formaldehyde (1.5 ml, 40% aq w/v, 0.02 mol) added with stirring. The mixture was kept at room temperature for 4½ hours, becoming turbid, then was poured into water and filtered. The filtrate was basified by addition of conc. ammonia to precipitate a gum which solidified on cooling in ice. The solid was collected and washed well with cold water, but reverted to a gum overnight.

This crude material (the title compound) was dissolved in refluxing propan-2-ol, filtered, cooled slightly and acidified with ethereal HCl. The solution was cooled in ice and the resulting solid collected and dried to give the title compound as the hydrochloride (0.98 g, 14.1% overall yield from original starting materials) m.p. 215°–216° C. Found C,62.26; H,7.16, N,7.73; $C_{20}H_{22}N_2O$. HCl ¼ $H_2O$ requires: C,69.15; H,6.82; N8.06%.

EXAMPLE 3

1-(5-Methoxyindol-3-ylmethyl)-4-hydroxy-4-(p-chlorophenyl) piperidine

The title compound may be obtained by substituting an equivalent amount of 5-methoxyindole for indole in the procedure of Example 1.

EXAMPLE 4

1-(2-Methylindol-3-ylmethyl)-4-hydroxy-4-(p-chlorophenyl) piperidine

The title compound may be obtained by substituting an equivalent amount of 2-metylindole for indole in the procedure of Example 1.

EXAMPLE 5

1-(5-Hydroxyindol-3-ylmethyl)-4-hydroxy-4-phenyl-piperidine

The title compound may be obtained by substituting an equivalent amount of 5-hydroxyindole for indole in the procedure of Example 2.

Pharmacological Evaluation

The compound of Example 1 was compared to haloperidol by the following test procedures.

Test 1 Inhibition of Amphetamine Induced Stereotypy

The compounds were tested according to the procedure of R. M. Quinton and G. Halliwell, Nature 200, 178-179 (1963). Rats were given test compounds an hour before 5 mg/kg d-amphetamine. Intensity of subsequent stereotyped behaviour of treated group was compared with that of control animals (vehicle+amphetamine).

Test 2 Inhibition of Apomorphine Induced Climbing

The method used was that described by Marcais H., Protais P., Costentin J. and Schwartz J. C. (1978). Psychopharmacology Vol 56 pp 233-234. Mice were given test compounds an hour before 10 mg/kg apomorphine. The mice were placed in small wire cages and subsequent climbing behaviour of treated and control groups compared. The doses shown are those calculated to reduce the climbing score of control animals by 50%.

Test 3 Inhibition of p-chloroamphetamine hyperactivity

Three groups of 4 female mice (20–24 g) received the test compounds (50 mg/kg po) and a fourth group the requisite volume of vehicle. Thirty minutes later all the animals are given 20 mg/kg p-chloroamphetamine (pCA) ip. The grouped mice are placed immediately in square plastic cages in activity monitors and their motor activity recorded over the period 10–30 minutes post pCA. This procedure is repeated three more times so that four groups of mice are used per treatment and each activity monitor is used with all treatments in turn. The inhibition of pCA induced hyperactivity is calculated thus:

$$(C-T)/C \cdot 100\%$$

where

C=mean activity of control groups 10–30 minutes post pCA.

T=mean activity of treated groups 10–30 minutes post pCA.

This test is used as an in vivo screen for detection of 5-hydroxytryptamine uptake inhibitors.

Compounds giving >50% inhibition are considered of special interest.

Test 4 Increase in Halothane Induced Sleep Time

Groups of 6 mice received the test compounds or the requisite volume of vehicle p.o. one hour before being placed in a perspex container. A gas mixture containing 3% halothane in oxygen was passed through this container for 5 minutes. Next the mice were removed and placed on their backs and the latency to the restoration of the righting reflex noted.

The doses shown are those calculated to increase the duration of halothane induced loss of righting reflex by 50%.

Test 5 Increase in Fall Rate From Revolving Drum

Groups of 8 mice were trained to walk on a slowly revolving horizontal drum prior to dosing with various concentrations of the test drugs or vehicle. An hour later the mice were replaced on the drum and the number of times each animal fell during the following 3 minutes was noted (mice were replaced immediately after each fall). Trained control mice did not fall. The doses shown are those calculated to induce a fall rate half that of the maximum theoretically possible. The results obtained comparing the compound of Example I with haloperidol shown in the following table.

TABLE I

| Test Procedure | $ED_{50}$ (mg/kg p.o.) Example 1(A) | $ED_{50}$ (mg/kg p.o.) Haloperidol (B) | A/B |
|---|---|---|---|
| 1. Inhibition of amphetamine induced stereotypy. | 25 | 0.7 | 36 |
| 2. Inhibition of apomorphine induced climbing. | 20 | 0.5 | 40 |
| 3. Inhibition of p-chloro amphetamine hyperactivity. | 10 | 0.3 | 33 |
| 4. Increase in halothane induced sleep time. | 200 | 0.2 | 1000 |
| 5. Increase in fall rate from revolving drum. | 50 | 0.9 | 56 |

It is considered that the antipsychotic activity of major tranquillizers (e.g. haloperidol) is related to their ability to inhibit dopamine receptors. The major side effects of these agents are sedation and their facility to induce extrapyramidal signs similar to those associated with parkinsonism.

Test 1, 2 and 3 are measures of dopamine antagonism. Test 4 is a measure of the sedative potential and 5 is a measure of the ability to induce extrapyramidal effects.

Thus the compound of Example 1 is a less potent dopamine antagonist than haloperidol but although haloperidol prolongs halothane-induced sleep at doses lower than those required to ihibit dopaminergic responses, the dose of compound Example 1 required to induce a similar effect is 8–20 times greater than those required to inhibit dopaminergic responses. Thus the sedative potential of the compound of Example 1 is lower than that of haloperidol and it also exhibits an advantage with regard to unwanted extrapyramidal effects.

Analogues of the compounds of Examples 1 and 2 having ethylene instead of methylene groups were prepared and tested for inhibition of amphetamine induced stereotypy and inhibition of pCA induced hyperactivity in tests 1 and 3 respectively already described above. These analogues are described in Examples 6 and 7 below and the results are given in Table 2 below.

EXAMPLE 6

1-(2-(Indol-3-yl)ethyl)-4-hydroxy-4-phenylpiperidine

A mixture of 3-(2-bromoethyl)indole(2.25 g; 0.011 M); 4-hydroxy-4-phenylpiperidine(1.77 g; 0.01 M), potassium carbonate (1.5 g) and dimethylformamide (20 ml) was stirred and heated in an oil-bath maintained at 75° for 20.5 hours under a nitrogen blanket. The mixture was poured onto water (100 ml) and cooled in ice to give a sticky yellow gum. The solvents were decanted and the gum washed by repeated decantation with a large volume of water. It was then dissolved in ethanol (25 ml), acidified with ethanolic HCl and the solvents evaporated. The residual gum was crystallised from EtOH/EtAc and the crystals were collected by filtration and washed with 1:1 ethanol/ethyl acetate and then with ethyl acetate.

The crude product was thoroughly triturated with ethanol/ethyl acetate, then crystallised from an EtOH-MeOH-H$_2$O-EtAc mixture with filtration to remove a little undissolved material. Cooling and filtration afforded the title compound as the hydrochloride, quaterhydrate (1.35 g; 37.4%) as colourless needles, mp 228°–230° (dec; decomposition occurred above 210°).

Tlc on silica showed clear signs of decomposition. Tlc on alumina was satisfactory.

Found C,69.92; H,7.14; N,7.44 C$_{21}$H$_{24}$N$_2$O,HCl.¼H$_2$O requires C,69.79; H,7.11; N,7.75%.

EXAMPLE 7

1-(2-(Indol-3-yl)ethyl)-4-(p-chlorophenyl)-4-hydroxypiperidine

A mixture of 3-(2-bromoethyl)indole (1.06 g; 4.73 mM), 4-(p-chlorophenyl)piperidin-4-ol (1.0 g; 4.72 mM), potassium carbonate (0.75 g; 5.42 mM) and dimethylformamide (12 ml) was stirred in an oil-bath maintained at 75° for 19.5 hours under a nitrogen blanket. The mixture was poured onto water (50 ml) and cooled in ice. The sticky, yellow solid which formed was filtered off and washed well with water. It was then promptly transferred to a new flask (the solid tended to gum) and dissolved in ethanol, acidified with ethanolic HCl and the solvents evaporated. The residue was crystallised from iso-propanol/ethyl acetate, then twice triturated well with ethanol/ethyl acetate. Filtration gave the title compound as the hydrochloride (0.99 g; 53.5%) as very pale pink plates, m.p. 248°–252° (dec; decomposition occurred above 235°).

Tlc on silica showed clear signs of decomposition; tlc on alumina was satisfactory but it was not possible to remove faint traces of base-line material.

Found C,64.24; H,6.20; N,6.79 C$_{21}$H$_{23}$ClN$_2$O,HCl requires C,64.45; H,6.18; N,7.16%.

TABLE 2

| Compound | ED$_{50}$ (mg/kg p.o.) | |
|---|---|---|
| | Inhibition of amphetamine induced stereotypy. | Inhibition of pCA induced hyperactivity |
| Example 2 | | 32.6 |
| Example 6 | >50 | >50 |
| Example 1 | 25 | 10 |
| Example 7 | >50 | >50 |

The results reported in Table 2 show that neither of the compounds of Examples 6 and 7 posses significant antagonist activity at dopaminergic reception at 50 mg/kg. In contrast the componds of Examples 1 and 2 both show activity with the compound of Example 1 being the more potent.

The invention includes a method for the treatment of psychoses in a mammal including schizophrenia which method comprises administering to said mammal an effective amount of a compound of formula II as described herein or a pharmaceutically acceptable salt thereof.

The amount of compound used will depend on the activity of the compound and the needs of the mammal being treated. Amounts may range from 1 to 100 mg/kg body weight e.g. from 5 to 25 mg/kg.

I claim:

1. A compound of the formula

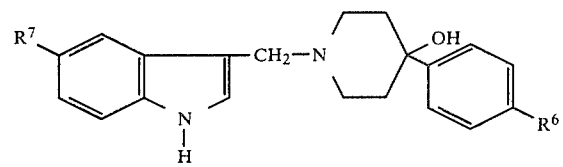

or a pharmaceutically acceptable salt thereof wherein R$^6$ represents hydrogen, halogen, trifluoromethyl or methyl and R$^7$ represents hydrogen, methyl, hydroxy or methoxy.

2. 1-(Indol-3-ylmethyl)-4-hydroxy-4-(p-chlorophenyl) piperidine or a pharmaceutically acceptable salt thereof.

3. 1-(Indol-3-ylmethyl)-4-hydroxy-4-phenylpiperidine or a pharmaceutically acceptable salt thereof.

4. A pharmaceutical composition for use in the treatment of psychoses comprising an effective amount of a compound of claim 1 and a pharmaceutically acceptable carrier.

5. A pharmaceutical composition as claimed in claim 4, wherein said compound is selected from 1-(indol-3-ylmethyl)-4-hydroxy-4-(p-chlorophenyl) piperidine and 1-(indol-3-ylmethyl)-4-hydroxy-4-phenylpiperidine or a pharmaceutically acceptable salt thereof.

6. A method for the treatment of psychoses in a mammal which method comprises administering to said mammal an effective amount of a compound as claimed in claim 1, or a pharmaceutically acceptable salt thereof.

7. A method as claimed in claim 6, wherein said compound is selected from 1-(indol-3-ylmethyl)-4-hydroxy-4-(p-chlorophenyl)piperidine and 1-(indol-3-ylmethyl)-4-hydroxy-4-phenylpiperidine or a pharmaceutically acceptable salt thereof.

* * * * *